United States Patent [19]

Koch et al.

[11] Patent Number: 5,009,493

[45] Date of Patent: Apr. 23, 1991

[54] MIRROR ARRANGEMENT FOR A BEAM PATH IN A MULTIPLE-REFLECTION MEASURING CELL

[75] Inventors: Edmund Koch; Dieter Pruss, both of Lübeck, Fed. Rep. of Germany

[73] Assignee: Drägerwerk Aktiengesellschaft, Lübeck, Fed. Rep. of Germany

[21] Appl. No.: 400,698

[22] Filed: Aug. 30, 1989

[30] Foreign Application Priority Data

Sep. 10, 1988 [DE] Fed. Rep. of Germany ....... 3830906

[51] Int. Cl.$^5$ .......................... G02B 5/08; G01N 21/00
[52] U.S. Cl. ..................................... 350/619; 350/622; 356/437; 356/439; 356/440; 356/442; 356/246
[58] Field of Search ................ 350/619, 622; 356/437, 356/439, 440, 442, 246; 250/343

[56] References Cited

U.S. PATENT DOCUMENTS

2,729,143  1/1956  White ................................. 250/343
3,748,014  7/1973  Beiser ................................ 350/619

FOREIGN PATENT DOCUMENTS

0871125  10/1981  U.S.S.R. .............................. 350/619
0894494  12/1981  U.S.S.R. .............................. 356/437
89/03028   4/1989  World Int. Prop. O. .......... 356/437

OTHER PUBLICATIONS

Shimizu et al.; "Stark Spectroscopy by 10-$\mu$ Lasers Using a Multipath Cell"; Journal of Applied Physics; vol. 46, No. 1, Jan. 1975, pp. 258–259.

"Minimization of Volume and Astigmatism in White Cells for Use with Circular Sources and Apertures" by W. Bruce Olson, Applied Optics, vol. 23, No. 10, May 15, 1984, pp. 1580–1585.

*Primary Examiner*—Bruce Y. Arnold
*Assistant Examiner*—R. D. Shafer
*Attorney, Agent, or Firm*—Walter Ottesen

[57] ABSTRACT

The invention is directed to a mirror arrangement for a beam path in a multiple-reflection cell for measuring the absorption of light in a measuring gas. In the measuring arrangement, an entrance aperture is imaged on an exit aperture via an entrance aperture mirror, a field mirror and an exit aperture mirror. This arrangement is improved in that the astigmatism of the imaging error is considerably reduced. For this purpose, the form of the aperture mirrors is approximately defined by an ellipsoid wherein the focal point spacing is approximately equal to half the distance between the entrance aperture and the exit aperture.

3 Claims, 1 Drawing Sheet

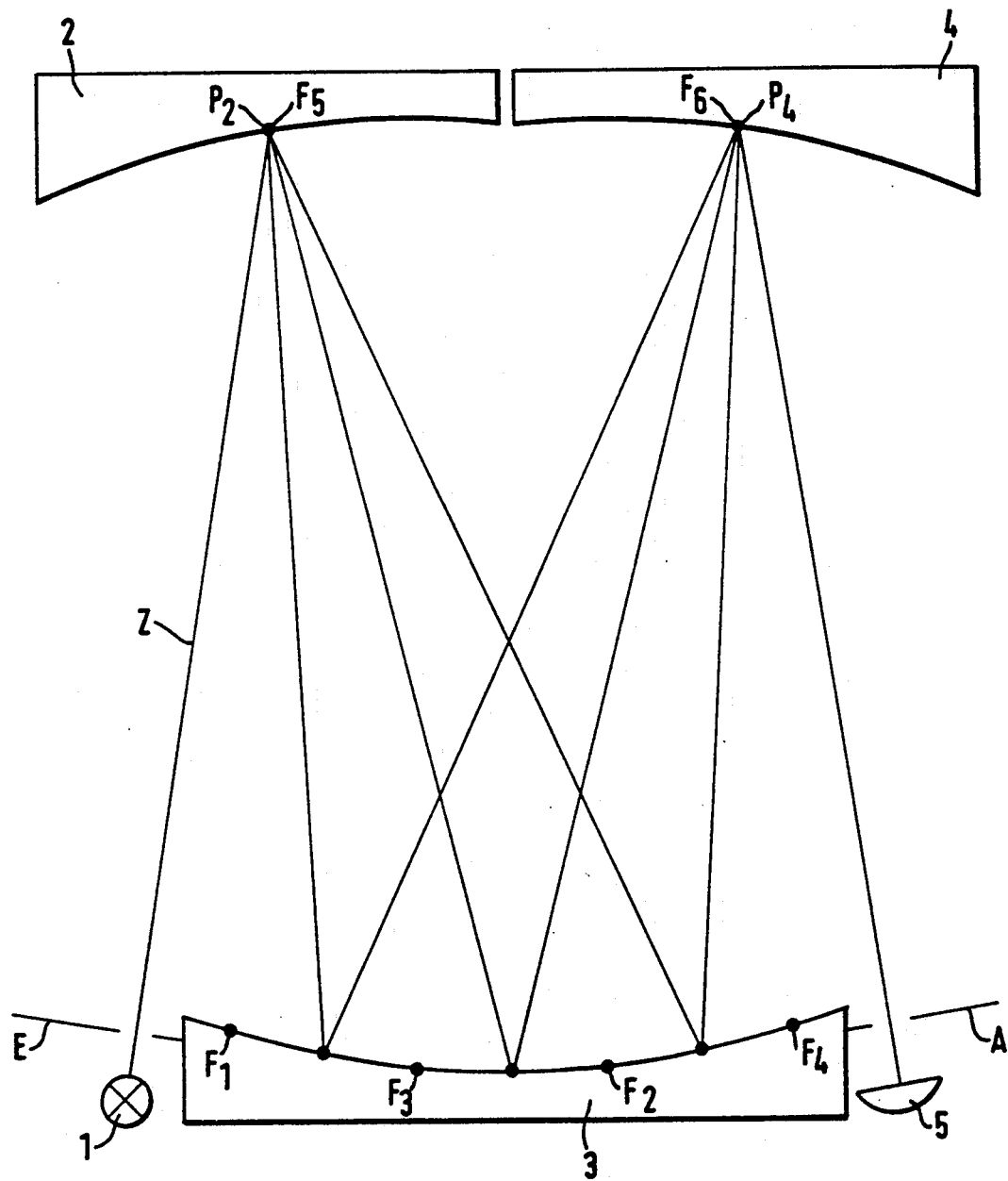

MIRROR ARRANGEMENT FOR A BEAM PATH IN A MULTIPLE-REFLECTION MEASURING CELL

Field of the Invention

The invention relates to a mirror arrangement for a beam path in a multiple-reflection cell for measuring the absorption of light in a measuring gas wherein an entrance aperture is imaged via an entry aperture mirror, a field mirror and an exit aperture mirror with multiple reflections onto an exit aperture.

Background of the Invention

Such measuring cells are used as measuring cuvettes for absorption of infrared radiation in a measuring gas, for example, and with small outer dimensions, permit an adequately long optical path length for the beam path. Such multiple-reflection cells are known as White cells.

A significant disadvantage of these white cells is the disturbing error of an imaging astigmatism while using spherical mirrors. Because of the desired small outer dimensions of a White cell, additional optical corrective lenses are undesired since they would lead to a loss of intensity. Furthermore, the astigmatic image is slightly curved and this curve cannot be fully compensated for. This subject matter is discussed in the paper entitled "Minimization of Volume and Astigmatism in White Cells for use with Circular Sources and Apertures" by W. Bruce Olson, Applied Optics, Volume 23, No. 10, May 15, 1984.

Summary of the Invention

It is an object of the invention to improve a mirror arrangement of the kind described above such that the astigmatic imaging error is considerably reduced.

The mirror arrangement of the invention defines a beam path in a multiple-reflection cell for measuring the absorption of light in a measuring gas, the cell having an entrance aperture and an exit aperture separated from each other by a predetermined distance. The mirror arrangement includes: an entrance aperture mirror and an exit aperture mirror having respective reflective surfaces approximating respective ellipsoids; the entrance aperture mirror defining first and second focal points ($F_1$, $F_2$) and the exit aperture mirror defining third and fourth focal points ($F_3$, $F_4$); a field mirror disposed opposite the aperture mirrors so as to define a beam path for a beam which permits the entrance aperture to be imaged into the exit aperture via the aperture mirrors and the field mirror; the first and second focal points ($F_1$, $F_2$) being separated by a first focal point spacing ($F_1$-$F_2$) and the third and fourth focal points ($F_3$, $F_4$) being separated by a second focal point spacing ($F_3$-$F_4$); and, the first and second focal point spacings ($F_1$-$F_2$ and $F_3$-$F_4$) having a sum which is approximately equal to the predetermined distance separating the entrance and exit apertures.

Thus, according to a feature of the invention, the form of the aperture mirrors is configured to approximate an ellipsoid with the focal point spacing being approximately equal to half the distance between the entrance aperture and the exit aperture.

By relativizing the focal point distance of the ellipsoid to the distance between the entrance aperture and the exit aperture, the astigmatic imaging errors for sequential imaging by means of the aperture mirrors are reduced to a value which is not disturbing.

In order to reduce the astigmatic imaging error of the entire mirror arrangement still further, it is advantageous to configure the field mirror in the form of an ellipsoid wherein the spacing of its two focal points is approximately equal to the spacing of the points of incidence of the central ray of a bundle of rays on the aperture mirror.

It is advantageous to configure the ellipsoid as a portion of a toroid in order to simplify the complex realization of an ellipsoid with the toroid having radii of curvature which are equal to those which determine the planar center point of the particular ellipsoid. To produce such a component portion from a toroid, the surface of the ellipsoid is first computed and the radii of curvature in the center point are determined. Thereafter, a corresponding toroid is formed from which equal component pieces can be carved out as the aperture mirrors.

One possibility of determining the center point of an ellipsoid is to determine the beam path of the central ray of a bundle of rays and to determine the planar center point as the point of incidence of the central ray on the ellipsoid surface.

Brief Description of the Drawing

The invention will now be described with reference to the drawings which shows a schematic of a preferred embodiment of the mirror arrangement according to the invention for a beam path in a multiple-reflection cell.

Description of the Preferred Embodiments of the Invention

A multiple-reflection cell is shown in the drawing with eight path segments. The beam path is represented by the central ray Z and originates at the light source 1. The beam path Z is guided through an entrance slit E and via several reflections at the entrance aperture mirror 2, field mirror 3 and exit aperture mirror 4. Thereafter, the beam path passes through the exit slit A to the detector 5.

The surfaces of the respective aperture mirrors (2, 4) ate configured so as to have an ellipsoidal form. Their respective focal point spacings ($F_1$-$F_2$) and ($F_3$-$F_4$) are so selected that their sum is approximately equal to the spacing between the entrance slit E and the exit slit A.

The field mirror 3 is likewise ellipsoidally configured with spacing ($F_5$-$F_6$) of both focal points being equal to the spacing between the incident points $P_2$ and $P_4$ of the central ray Z on the aperture mirrors (2, 4).

It is understood that the foregoing description is that of the preferred embodiments of the invention and that various changes and modifications may be made thereto without departing from the spirit and scope of the invention as defined in the appended claims.

What is claimed is

1. A mirror arrangement for defining a beam path in a multiple-reflection cell for measuring the absorption of light in a measuring gas, the cell having an entrance aperture and an exit aperture separated from each other by a predetermined distance, the mirror arrangement comprising:

an entrance aperture mirror and an exit aperture mirror having respective reflective surfaces approximating respective ellipsoids;

said entrance aperture mirror defining first and second focal points ($F_1$, $F_2$) and said exit aperture mirror defining third and fourth focal points ($F_3$, $F_4$);

a field mirror disposed opposite of and at a confocal distance from each of said aperture mirrors so as to define a beam path for a beam which permits said entrance aperture to be imaged into said exit aperture via said aperture mirrors and said field mirror;

said entrance aperture and said exit aperture being disposed at opposite ends of said field mirror;

said first and second focal points ($F_1$, $F_2$) being separated by a first focal point spacing ($F_1$-$F_2$) and said third and fourth focal points ($F_3$, $F_4$) being separated by a second focal point spacing ($F_3$-$F_4$); and, said first and second focal point spacings ($F_1$-$F_2$ and $F_3$-$F_4$) having a sum which is approximately equal to said predetermined distance.

2. The mirror arrangement of claim 1, said field mirror having a reflective field mirror surface corresponding to an ellipsoidal surface, said field mirror surface defining fifth and sixth focal points ($F_5$, $F_6$) disposed at a third focal point spacing ($F_5$-$F_6$) from each other; said beam being a bundle of rays with one of said rays being a central ray having respective incidence points ($P_2$, $P_4$) on said aperture mirrors; and, said incidence points being separated by a spacing equal to said third focal point spacing ($F_5$-$F_6$).

3. The mirror arrangement of claim 1, said aperture mirrors being component portions of a toroid having respective radii of curvature which determine the respective planar center points of said aperture mirrors.

* * * * *

UNITED STATES PATENT AND TRADEMARK OFFICE
CERTIFICATE OF CORRECTION

PATENT NO. : 5,009,493
DATED : April 23, 1991
INVENTOR(S) : Edmund Koch and Dieter Pruss It is certified that error appears in the above-identified patent and that said Letters Patent is hereby corrected as shown below:

In column 1, line 19: delete "white" and substitute -- White -- therefor.

In column 2, line 25, delete "drawings" and substitute -- drawing -- therefor.

In column 2, line 42: delete "ate" and substitute -- are -- therefor.

Signed and Sealed this

Second Day of November, 1993

Attest:

BRUCE LEHMAN

*Attesting Officer*   *Commissioner of Patents and Trademarks*